US012729179B2

(12) United States Patent
Yu et al.

(10) Patent No.: US 12,729,179 B2
(45) Date of Patent: Sep. 8, 2026

(54) PREPARATION METHOD OF SULFUR-CONTAINING BIPHENYL COMPOUND

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Haibo Yu, Shenyang (CN); Hao Yang, Shenyang (CN); Guimin Zhao, Shenyang (CN); Zhongbao Ren, Shenyang (CN); Hongfei Wu, Shenyang (CN); Xueling Wang, Shenyang (CN); Zeyong Zhang, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 598 days.

(21) Appl. No.: 17/287,460

(22) PCT Filed: Oct. 8, 2019

(86) PCT No.: PCT/CN2019/109858
§ 371 (c)(1),
(2) Date: Apr. 21, 2021

(87) PCT Pub. No.: WO2020/083018
PCT Pub. Date: Apr. 30, 2020

(65) Prior Publication Data

US 2021/0380530 A1 Dec. 9, 2021

(30) Foreign Application Priority Data

Oct. 25, 2018 (CN) ........................ 201811250209.8

(51) Int. Cl.
*C07C 319/20* (2006.01)
*B01J 23/06* (2006.01)
*B01J 31/24* (2006.01)

(52) U.S. Cl.
CPC ............. *C07C 319/20* (2013.01); *B01J 23/06* (2013.01); *B01J 31/2409* (2013.01); *B01J 2531/847* (2013.01)

(58) Field of Classification Search
CPC ..... C07C 319/20; B01J 23/06; B01J 31/2409; B01J 2531/847; A01N 31/08; A01N 41/10; A01P 7/02
See application file for complete search history.

(56) References Cited

U.S. PATENT DOCUMENTS 4,263,466 A * 4/1981 Colon et al. .............. C07C 1/26 585/421
9,856,212 B1 * 1/2018 Zhang et al. ......... C07C 323/09

FOREIGN PATENT DOCUMENTS

CN 101870681 A 10/2010
CN 105541682 A 5/2016
WO 2013027660 A1 2/2013
WO 2014202505 A1 12/2014

OTHER PUBLICATIONS

J. Org. Chem. 2017, 82, 9931-9936 (Batesky et al.) (Year: 2017).*
Organometallics_2017_36_1662-1672 (Bajo et al.) (Year: 2017).*
RSC_Adv_2016_6_62208-62217 (Jayabharathi et al.) (Year: 2016).*

* cited by examiner

*Primary Examiner* — Amy C Bonaparte
*Assistant Examiner* — Derek Rhoades
(74) *Attorney, Agent, or Firm* — NKL Law; Allen Xue

(57) ABSTRACT

A preparation method of a sulfur-containing biphenylsulfur-containing biphenyl compound shown by the general formula (I) has a reaction formula as follows:

(II)

(I)

Each substituent in the formula is defined in the description. In the method, halogeno benzene shown by the general formula (II) generates a coupling reaction in a catalytic system composed of a nickel compound and at least one ligand under the combined action of metallic zinc to obtain the sulfur-containing biphenyl compound shown by the general formula (I).

11 Claims, No Drawings

PREPARATION METHOD OF SULFUR-CONTAINING BIPHENYL COMPOUND

TECHNICAL FIELD

The present invention belongs to the field of organic synthesis, and particularly relates to a preparation method of a sulfur-containing biphenyl compound.

BACKGROUND

The sulfur-containing biphenyl compound is a novel efficient acaricide. CN105541682A discloses the sulfur-containing biphenyl compound shown by a formula I. The compound has excellent acaricidal activity against *Tetranychus cinnabarinus*. CN105541682A reports the synthetic method of the compound. Aryl iodobenzene and bis(pinacolato)diboron are coupled with a palladium catalyst in an appropriate organic solvent under the action of appropriate alkali to obtain a target object. The specific reaction formula is as follows:

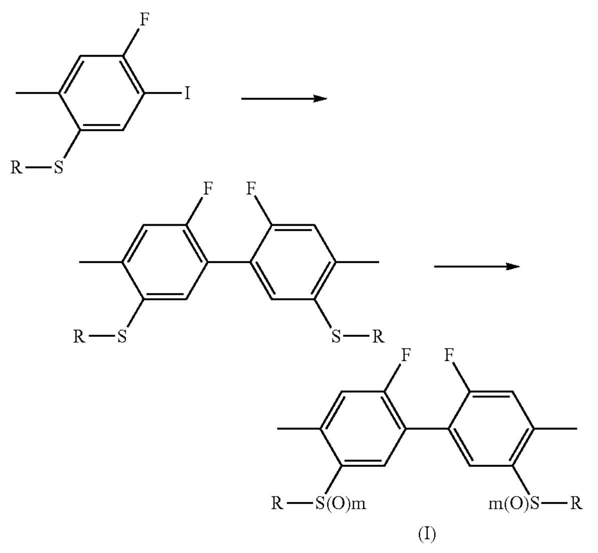

(I)

The technicians continuously make efforts to research and develop more advanced and favourable, and more environmentally friendly novel methods for preparing the highly effective and safe sulfur-containing biphenyl acaricides with higher quality and lower cost.

SUMMARY

The purpose of the present invention is to provide a preparation method of a sulfur-containing biphenyl compound, which is suitable for large-scale industrial production.

To achieve the above purpose, the present invention adopts the following technical solution:

A preparation method of a sulfur-containing biphenyl compound is provided. The method of the sulfur-containing biphenyl compound shown by general formula (I) has a reaction formula as follows:

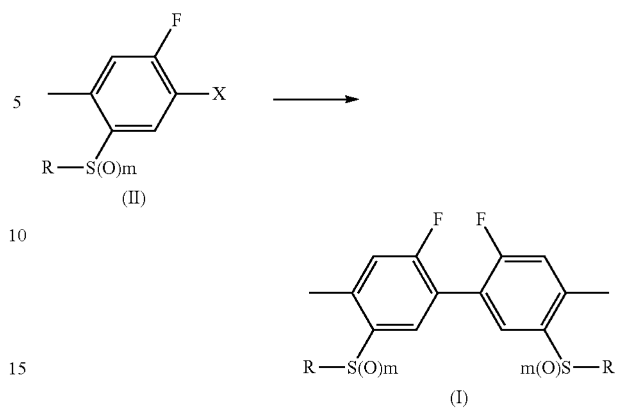

(II)

(I)

In the formula: R is selected from $C_1$-$C_8$ alkyl, $C_1$-$C_8$ haloalky, $C_2$-$C_8$ alkenyl, $C_2$-$C_8$ haloalkenyl, $C_2$-$C_8$ alkynyl, $C_2$-$C_8$ haloalkynyl; X is selected from chlorine or bromine; and m is selected from 0, 1 or 2.

The compound shown by the general formula (II) generates a coupling reaction in a catalytic system composed of a nickel compound and at least one ligand under the combined action of metallic zinc to obtain the compound shown by the general formula (I).

Reaction conditions are: the compound shown by the general formula (II), the nickel compound, the ligand and the metallic zinc generate the coupling reaction for 1-24 hours in a suitable solvent at a temperature of 20° C. to a boiling point of the selected solvent, to obtain the compound shown by the general formula (I).

The solvent is selected from toluene, ethyl acetate, acetonitrile, tetrahydrofuran, dioxane, acetone, butanone, dimethyl formamide or dimethyl sulfoxide.

An activation additive is added in the coupling reaction, and the addition amount of the activation additive is 1%-15% of the molar weight of the compound shown by the general formula (II), wherein the activation additive is metal halide, metal sulfate or metal phosphate, and the metal mentioned in the activation additive is alkali metal, alkaline earth metal, manganese or aluminum.

The nickel compound is selected from nickel chloride, nickel bromide, bis(triphenylphosphine) nickel chloride or bis(triphenylphosphine) nickel bromide; the addition amount of the nickel compound is 1%-10% of the molar weight of the compound shown by the general formula (II); the ligand is selected from triarylphosphine, wherein aryl is selected from $C_6$-$C_{34}$ aryl; the addition amount of the ligand is 20%-100% of the molar weight of the compound shown by the general formula (II); and the amount of the metallic zinc is 50%-200% of the molar weight of the compound shown by the general formula (II).

The nickel compound is selected from nickel chloride; the addition amount of the nickel compound is 2%-5% of the molar weight of the compound shown by the general formula (II); the ligand is selected from triphenylphosphine; the addition amount of the ligand is 40%-60% of the molar weight of the compound shown by the general formula (II); the activation additive is selected from halogenated substances of alkali metal; the addition amount of activation additive is 5%-10% of the molar weight of the compound shown by the general formula (II); and the amount of the metallic zinc is 100%-150% of the molar weight of the compound shown by the general formula (II).

The activation additive is selected from sodium bromide, potassium bromide, sodium iodide or potassium iodide.

Further, in the reaction formula of the above preparation method, R is selected from methyl, ethyl, cyclopropyl, trifluoromethyl, $CH_2CF_3$, $CH_2CHF_2$, $CH_2CH_2F$, $CH_2CH{=}CF_2$ or $CH_2CN$; X is selected from chlorine or bromine; when m is selected from 0 or 1, the nickel compound is selected from nickel chloride or nickel bromide; the activation additive is selected from alkali metal halide; and the ligand is selected from triphenylphosphine.

Furthermore, in the reaction formula of the above preparation method, R is selected from $CH_2CF_3$; X is selected from chlorine; when m is independently selected from 0, the nickel compound is selected from nickel chloride; the activation additive is selected from sodium bromide, potassium bromide, sodium iodide or potassium iodide; and the ligand is selected from triphenylphosphine.

Moreover, the preparation of the substituted chloro benzene or bromo benzene in the compound shown by the general formula (II) can be found in the method described in WO2014202505A1.

Meanwhile, when m=1 or 2 in the reaction formula in the above preparation process, the compound shown by the general formula (I) is a sulfoxide or sulfone compound, which can also be prepared by the reaction of biphenyl sulfide compound (m=0) prepared by the above method with an appropriate oxidant, wherein the appropriate oxidant is selected from peroxybenzoic acid, hydrogen peroxide or (meta) sodium periodate.

In the synthetic methods provided above and the definitions of groups in the compounds of the formulas, the terms used in the collection are generally defined as follows:

Alkyl refers to linear or branched groups such as methyl, ethyl, n-propyl, isopropyl, n-butyl, isobutyl, sec-butyl, tert-butyl, n-pentyl and isopentyl. Cycloalkyl refers to groups in the form of cyclic chain, such as cyclopropyl, cyclobutyl, cyclopentyl, cyclohexyl, methylcyclopropyl and cyclopropylcyclopropyl. Alkenyl refers to linear or branched alkenyl, such as 1-propenyl, 2-propenyl and different butenyl and pentenyl isomers. Halogen refers to fluorine, chlorine, bromine and iodine.

Compared with the prior art, the present invention has the following advantages:

The sulfur-containing biphenyl compound shown by general formula (I) in the present invention is a novel efficient and safe acaricide. In order to find a method applicable to large-scale industrial production of the sulfur-containing biphenyl compound, the present invention uses cheap and readily-available chlorobenzene or bromobenzene as raw material to replace the original iodobenzene. The low-price nickel compound is used as the catalyst to replace the expensive palladium catalyst. Therefore, the new method of the present invention is more suitable for large-scale industrial production.

EXAMPLES

The following Examples are used to describe the preparation method of the general formula (I) shown in the present invention in detail, but are not used to limit the present invention. Various changes and modifications can be made within the scope defined by the claims of the present invention.

In the preparation process of the present invention, the substituted chlorobenzene or bromobenzene is coupled with cheap metallic zinc in a catalytic system composed of a cheap nickel compound and an organic phosphine ligand to prepare a sulfur-containing biphenyl compound shown by the general formula (I).

Example 1

Synthesis of 2,2'-difluoro-4,4'-dimethyl-5,5'-bis(2,2,2-trifluoroethylthio)-1,1'-biphenyl

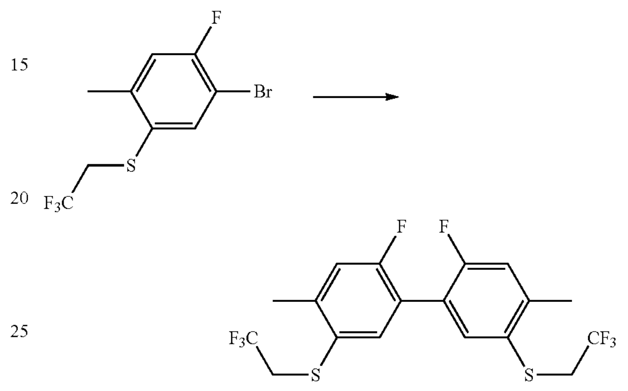

Triphenylphosphine (13.23 g, 0.05 moL), sodium bromide (1.55 g, 0.015 moL), zinc powder (6.56 g, 0.1 moL) and nickel chloride (0.65 g, 0.005 moL) were added to a reaction flask. Nitrogen was introduced to replace the air. Under the conditions of room temperature and nitrogen protection, 12.5 mL of DMF was dropped into the reaction flask for 5 min without stirring; the material partially turned red; then, 50 mL of DMF was added. The reaction mixture was heated to 60° C. and stirred for 1 h. A mixture (30.9 g, dissolved in 15 mL of DMF) of 2-fluoro-4-methyl-5-trifluoroethylthiobromobenzene (30.9 g, 0.1 moL) and DMF was added dropwise for about 2 h. After adding, the temperature was kept at 40-45° C. until the reaction was completed. After the reaction was ended, the reaction mixture was cooled and filtered (under filtration aiding by diatomite). After the filtrate was concentrated under reduced pressure, 50 mL of toluene and 50 mL of water were added, and the mixture was stood for layering. An organic layer was transferred to a reaction flask and cooled in ice water bath. Hydrogen peroxide (5.7 g, 0.05 moL) was added dropwise into the organic layer for about 0.5 h. After adding, the temperature was kept at 40° C. for 1 h, and the reaction mixture was sampled and analyzed. When the triphenylphosphine completely converted into triphenylphosphine oxide, the temperature was cooled to room temperature, then the triphenylphosphine oxide was filtered out. The filter cake was washed with toluene (15 mL), the filtrate was layered. The toluene was removed under reduced pressure, then added 15 g of ethanol, the temperature was increased until all solids were dissolved, the solution was cooled with ice water bath to be below 10° C. The solids were continuously precipitated out, then filtered and dried to obtain 19.15 g of target compound which is white solid, with a melting point of 64.2-65.1° C. The HPLC quantitative content is 99%, and the yield is 85%. $^1H$ NMR (300 MHz, $CDCl_3$): 7.55 (t, 2H), 7.06 (t, 2H), 3.33 (q, 4H), 2.52 (s, 6H). [M]=446.6 (GC-MS).

Example 2

Synthesis of 2,2'-difluoro-4,4'-dimethyl-5,5'-bis(2,2,2-trifluoroethylthio)-1,1'-biphenyl

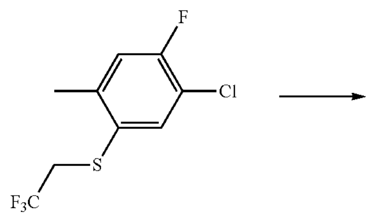

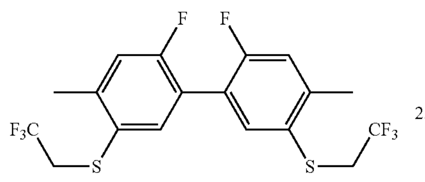

Triphenylphosphine (13.23 g, 0.05 moL), potassium iodide (1.64 g, 0.01 moL), zinc powder (6.56 g, 0.1 moL) and nickel chloride (0.65 g, 0.005 moL) were added to the reaction flask. Nitrogen was introduced to replace the air. Under the conditions of room temperature and nitrogen protection, 12.5 mL of DMF was dropped into the reaction flask for 5 min without stirring; the material partially turned red; then, 50 mL of DMF was added. The reaction mixture was heated to 40° C. and stirred for 1 h. A mixture (26.1 g, dissolved in 15 mL of DMF) of 2-fluoro-4-methyl-5-trifluoroethylthiochlorobenzene (26.1 g, 0.1 moL) and DMF was added dropwise for about 2 h. After adding, the temperature was kept at 55-60° C. until the reaction was completed. After the reaction was ended, the reaction mixture was cooled and filtered (under filtration aiding by diatomite). After the filtrate was concentrated under reduced pressure, 50 mL of toluene and 50 mL of water were added, and the mixture was stood for layering. An organic layer was transferred to a reaction flask and cooled in ice water bath. Hydrogen peroxide (5.7 g, 0.05 moL) was added dropwise into the organic layer for about 0.5 h. After adding, the temperature was kept at 40° C. for 1 h, and the reaction mixture was sampled and analyzed. When the triphenylphosphine completely converted into triphenylphosphine oxide, the temperature was cooled to room temperature, then the triphenylphosphine oxide was filtered out. The filter cake was washed with toluene (15 mL), the filtrate was layered. The toluene was removed under reduced pressure, then added 14 g of ethanol, the temperature was increased until all solids were dissolved, the solution was cooled with ice water bath to be below 10° C. The solids were continuously precipitated out, then filtered and dried to obtain 18.66 g of target compound which is white solid, with a melting point of 64.2-65.1° C. The HPLC quantitative content is 98%, and the yield is 82%. $^{1}H$ NMR (300 MHz, $CDCl_3$): 7.55 (t, 2H), 7.06 (t, 2H), 3.33 (q, 4H), 2.52 (s, 6H). [M]=446.6 (GC-MS).

Example 3

Synthesis of 2,2'-difluoro-4,4'-dimethyl-5,5'-bis(2,2,2-trifluoroethylthio)-1,1'-biphenyl

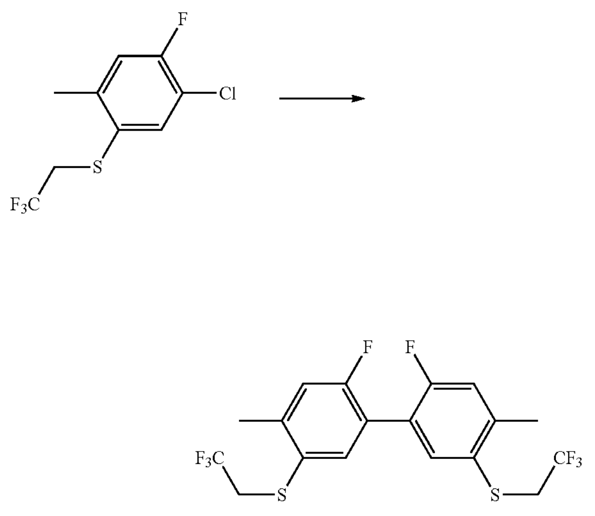

Triphenylphosphine (13.23 g, 0.05 moL), sodium iodide (0.75 g, 0.005 moL), zinc powder (6.56 g, 0.1 moL) and nickel bromide (1.09 g, 0.005 moL) were added into the reaction flask. Nitrogen was introduced to replace the air. Under the conditions of room temperature and nitrogen protection, 12.5 mL of DMF was dropped into the reaction flask for 5 min without stirring; the material partially turned red; then, 50 mL of DMF was added. The reaction mixture was heated to 40° C. and stirred for 1 h. A mixture (26.1 g, dissolved in 15 Ml of DMF) of 2-fluoro-4-methyl-5-trifluoroethylthiochlorobenzene (26.1 g, 0.1 moL) and DMF was added dropwise for about 2 h. After adding, the temperature was kept at 50-55° C. until the reaction was completed. After the reaction was ended, the reaction mixture was cooled and filtered (under filtration aiding by diatomite). After the filtrate was concentrated under reduced pressure, 50 mL of toluene and 50 mL of water were added, and the mixture was stood for layering. An organic layer was transferred to a reaction flask and cooled in ice water bath. Hydrogen peroxide (5.7 g, 0.05 moL) was added dropwise into the organic layer for about 0.5 h. After adding, the temperature was kept at 40° C. for 1 h, and the reaction mixture was sampled and analyzed. When the triphenylphosphine completely converted into triphenylphosphine oxide, the temperature was cooled to room temperature, then the triphenylphosphine oxide was filtered out. The filter cake was washed with toluene (15 mL), the filtrate was layered. The toluene was removed under reduced pressure, then added 15 g of ethanol, the temperature was increased until all solids were dissolved, the solution was cooled with ice water bath to be below 10° C. The solids were continuously precipitated out, then filtered and dried to obtain 18.90 g of target compound which is white solid, with a melting point of 64.2-65.1° C. The HPLC quantitative content is 98%, and the yield is 83%. $^{1}H$ NMR (300 MHz, $CDCl_3$): 7.55 (t, 2H), 7.06 (t, 2H), 3.33 (q, 4H), 2.52 (s, 6H). [M]=446.6 (GC-MS).

Example 4

Synthesis of 2,2'-difluoro-4,4'-dimethyl-5,5'-bis(2,2,2-trifluoroethylthio)-1,1'-biphenyl

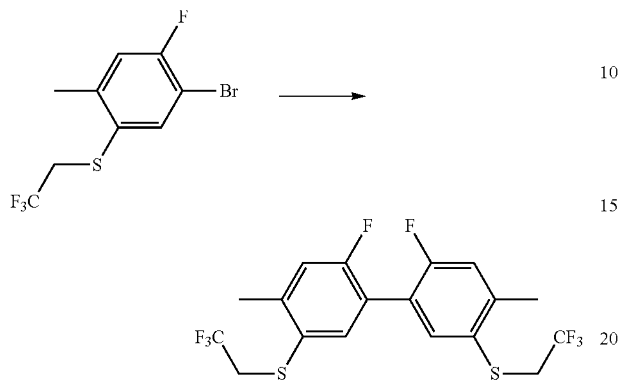

Triphenylphosphorus (534.7 g, 2 moL), sodium bromide (42.04 g, 0.4 moL), zinc powder (265.3 g, 4 moL) and nickel chloride (18.13 g, 0.14 moL) were added into the reaction flask. Nitrogen was introduced to replace the air. Under the conditions of room temperature and nitrogen protection, 1200 mL of DMF was dropped into the reaction flask for 30 min without stirring; the material partially turned red; then, 1200 mL of DMF was added. The reaction mixture was heated to 60° C. and stirred for 1 h. A mixture (1236 g, dissolved in 600 mL of DMF) of 2-fluoro-4-methyl-5-trifluoroethylthiobromobenzene (1236 g, 4 moL) and DMF was added dropwise for about 2 h. After adding, the temperature was kept at 40-45° C. until the reaction was completed. After the reaction was ended, the reaction mixture was cooled and filtered (under filtration aiding by diatomite). After the filtrate was concentrated under reduced pressure, 3000 mL of toluene and 2500 mL of water were added, and the mixture was stood for layering. An organic layer was transferred to a reaction flask and cooled in ice water bath. Hydrogen peroxide (226.7 g, 2 moL) was added dropwise into the organic layer for about 2 h. After adding, the temperature was kept at 40° C. for 1 h, and the reaction mixture was sampled and analyzed. When the triphenylphosphine completely converted into triphenylphosphine oxide, the temperature was cooled to room temperature, then the triphenylphosphine oxide was filtered out. The filter cake was washed with toluene (500 mL), the filtrate was layered. The toluene was removed under reduced pressure, then added 700 g of ethanol, the temperature was increased until all solids were dissolved, the solution was cooled with ice water bath to be below 10° C. The solids were continuously precipitated out, then filtered and dried to obtain 787.1 g of target compound which is white solid, with a melting point of 64.2-65.1° C. The HPLC quantitative content is 98.6%, and the yield is 87%. $^1H$ NMR (300 MHz, $CDCl_3$): 7.55 (t, 2H), 7.06 (t, 2H), 3.33 (q, 4H), 2.52 (s, 6H). [M]=446.6 (GC-MS).

Meanwhile, according to the above specific preparation method, other compounds in Table 1 below can be prepared only by replacing some conditions. Specifically, the nickel compound is selected from nickel chloride or nickel bromide; the activation additive is selected from alkali metal halide; and the ligand is selected from triphenylphosphine.

TABLE 1

Structures of Part of Compounds of Formula (I)

| Compound | $R_1$ | m |
|---|---|---|
| 1 | $CF_3$ | 0 |
| 2 | $CF_3$ | 1 |
| 3 | $CF_3$ | 2 |
| 4 | $CH_3$ | 0 |
| 5 | $CH_3$ | 1 |
| 6 | $CH_3$ | 2 |
| 7 | $CH_2CH_3$ | 0 |
| 8 | $CH_2CH_3$ | 1 |
| 9 | $CH_2CH_2F$ | 0 |
| 10 | $CH_2CH_2F$ | 1 |
| 11 | $CH_2CHF_2$ | 0 |
| 12 | $CH_2CHF_2$ | 1 |
| 13 | $CH_2CHF_2$ | 2 |
| 14 | $CH_2CF_3$ | 0 |
| 15 | $CH_2CF_3$ | 1 |
| 16 | $CH_2CF_3$ | 2 |
| 17 | $CF_2CHF_2$ | 0 |
| 18 | $CF_2CHF_2$ | 1 |
| 19 | $CF_2CHF_2$ | 2 |
| 20 | $CH_2CH_2CF_3$ | 0 |
| 21 | $CH_2CH_2CF_3$ | 1 |
| 22 | $CH_2CH_2CF_3$ | 2 |
| 23 | $CH_2CF_2CHF_2$ | 0 |
| 24 | $CH_2CF_2CHF_2$ | 1 |
| 25 | $CH_2CF_2CHF_2$ | 1 |
| 26 | $CH_2CF_2CF_3$ | 0 |
| 27 | $CH_2CF_2CF_3$ | 1 |
| 28 | $CH_2CF_2CF_3$ | 2 |
| 29 | $CF_2CHFCF_3$ | 0 |
| 30 | $CF_2CHFCF_3$ | 1 |
| 31 | $CF_2CHFCF_3$ | 2 |
| 32 | $CH_2CF_2CF_2CF_3$ | 0 |
| 33 | $CH_2CF_2CF_2CF_3$ | 0 |
| 34 | $CH_2CF_2CF_2CF_3$ | 1 |
| 35 | $CH_2CF_2CF_2CF_2CF_3$ | 0 |
| 36 | $CH_2CF_2CF_2CF_2CF_3$ | 1 |
| 37 | $CH_2CF_2CF_2CF_2CF_3$ | 2 |
| 38 | $CH_2CF_2CF_2CF_2CF_2CF_3$ | 0 |
| 39 | $CH_2CF_2CF_2CF_2CF_2CF_3$ | 1 |
| 40 | $CH_2CF_2CF_2CF_2CF_2CF_3$ | 2 |
| 41 | 3, 4, 4-trifluorobut-3-en-1-yl | 0 |
| 42 | 3, 4, 4-trifluorobut-3-en-1-yl | 1 |

The invention claimed is:

1. A preparation method of a sulfur-containing biphenyl compound, comprising:

conducting a coupling reaction of a compound of formula (II) to obtain the sulfur-containing biphenyl compound of formula (I) as shown in a reaction scheme below:

(II)

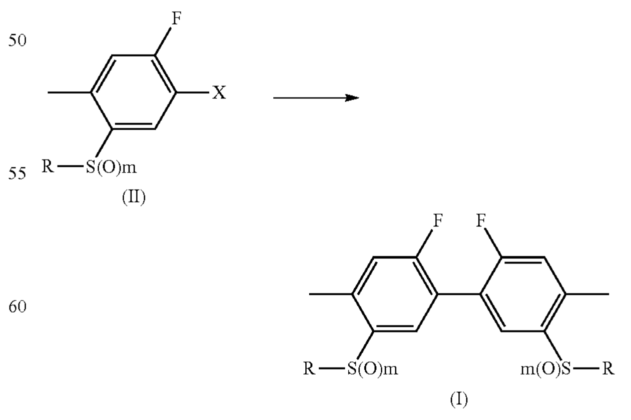

(I)

wherein R is $C_1$-$C_8$ alkyl or $C_1$-$C_8$ haloalkyl, X is bromine, and m is 0, wherein the reaction is carried out in a reaction mixture comprising a nickel compound, triarylphosphine, metallic zinc, and an activation additive, wherein the activation additive is sodium bromide, wherein the nickel compound is nickel chloride or nickel bromide, and wherein a yield of the sulfur-containing biphenyl compound is 82%-87%.

2. The preparation method according to claim 1, wherein in the coupling rection, the compound of formula (II), the nickel compound, triarylphosphine, the activation additive, and the metallic zinc react for 1-24 hours in a solvent at a temperature of 20° C. to a boiling point of the solvent to obtain the compound of formula (I).

3. The preparation method according to claim 2, wherein the solvent is selected from toluene, ethyl acetate, acetonitrile, tetrahydrofuran, dioxane, acetone, butanone, dimethyl formamide, and dimethyl sulfoxide.

4. The preparation method according to claim 1, wherein an amount of activation additive is 1%-15% of a molar weight of the compound of formula (II).

5. The preparation method according to claim 1, wherein the nickel compound is nickel chloride and the amount of the nickel compound is 2%-5% of the molar weight of the compound of formula (II).

6. The preparation method according to claim 1, wherein the amount of triarylphosphine is 20%-100% of a molar weight of the compound of formula (II).

7. The preparation method according to claim 6, wherein the amount of triarylphosphine is 40-60% of the molar weight of the compound of formula (II).

8. The preparation method according to claim 1, wherein the amount of the activation additive is 5%-10% of a molar weight of the compound of formula (II).

9. The preparation method according to claim 1, wherein an amount of the metallic zinc is 50-200% of a molar weight of the compound of formula (II).

10. The preparation method according to claim 1, wherein the amount of the metallic zinc is 100-150% of the molar weight of the compound of formula (II).

11. The preparation method according to claim 1, further comprising:

filtering and concentrating the reaction mixture to obtain a first liquid phase;

adding a first organic solvent and water to the first liquid phase;

obtaining a first organic phase from the third liquid phase after standing;

adding hydrogen peroxide into the organic phase to oxidize triarylphosphine to obtain triarylphosphine oxide and precipitating triarylphosphine oxide from the organic phase, filtering the organic phase to obtain a filter cake;

washing the filter cake with a second organic solvent to obtain a filtrate;

removing the second organic solvent from the filtrate by evaporation to obtain a residue;

adding ethanol to the residue to obtain a solution; and cooling the solution to precipitate the sulfur-containing biphenyl compound.

* * * * *